United States Patent

Boehmke et al.

Patent Number: 4,458,080
Date of Patent: Jul. 3, 1984

[54] IMIDAZOLINE DERIVATIVES

[75] Inventors: Günther Boehmke, Leverkusen, Fed. Rep. of Germany; Klaus-Dieter Bode, deceased, late of Odenthal, Fed. Rep. of Germany, by Selma Bode, sole heiress; Wilfried Kortmann, Hagen, Fed. Rep. of Germany

[73] Assignee: Bayer Aktiengesellschaft, Leverkusen, Fed. Rep. of Germany

[21] Appl. No.: 415,630

[22] Filed: Sep. 7, 1982

[30] Foreign Application Priority Data

Sep. 17, 1981 [DE] Fed. Rep. of Germany ....... 3137044

[51] Int. Cl.³ .............................................. C07D 233/18
[52] U.S. Cl. ..................................... 548/354; 8/115.5; 69/21; 162/158; 252/301.21
[58] Field of Search ........................................... 548/354

[56] References Cited

U.S. PATENT DOCUMENTS

| | | | |
|---|---|---|---|
| 2,794,808 | 6/1957 | Albrecht | 548/354 |
| 3,060,182 | 10/1962 | Zech | 548/354 X |
| 3,455,940 | 7/1969 | Stecker | 546/337 |
| 3,855,235 | 12/1974 | McConnell | 548/349 |
| 4,267,350 | 5/1981 | Tomalia et al. | 548/354 |

FOREIGN PATENT DOCUMENTS 1619078 10/1969 Fed. Rep. of Germany ...... 548/354

OTHER PUBLICATIONS

Butler, R., et al., J. Chem. Research(s), 1981, pp. 84, 85.

*Primary Examiner*—Richard A. Schwartz
*Attorney, Agent, or Firm*—Sprung, Horn, Kramer & Woods

[57] ABSTRACT

Imidazoline derivatives of the formula

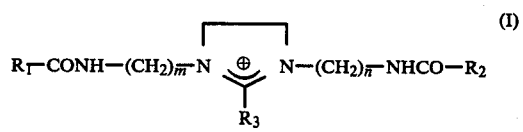

in which
$R_1$, $R_2$ and $R_3$ designate $C_1$-$C_{19}$-alkyl or $C_2$-$C_{19}$-alkenyl,
m and n designate 2 or 3, and
$A^\ominus$ designates an anion, in particular formate, acetate, phosphate, phosphite, phosphonate, sulphonate, toluenesulphonate or benzoate, a process for their preparation, and their use as softeners.

2 Claims, No Drawings

IMIDAZOLINE DERIVATIVES

The invention relates to imidazoline derivatives of the formula $$R_1-CONH-(CH_2)_m-N\overset{\oplus}{\underset{R_3}{\diagdown N}}-(CH_2)_n-NHCO-R_2 \quad A^{\ominus} \quad (I)$$

in which
$R_1$, $R_2$ $R_3$ designate $C_1$-$C_{19}$-alkyl or $C_2$-$C_{19}$-alkenyl,
m and n designate 2 or 3, and
$A^{\ominus}$ designates an anion, in particular formate, acetate, phosphate, phosphite, phosphonate, sulphonate, toluenesulphonate or benzoate.

Examples of suitable radicals $R_1$, $R_2$ and $R_3$ are $CH_3(CH_2)_{16}$ and $CH_3(CH_2)_{14}$; $R_3$ can in particular also represent $CH_3$.

The preparation of the new compounds can be effected, for example, in the following manner: compounds of the formula $$R_1-CONH-(CH_2)_m-NH-CH_2-CH_2-NH-(CH_2)_n-NHCO-R_2 \quad (II)$$

in which $R_1$, $R_2$, m and n have the meanings given for formula I,
are acylated using acylating agents of the formula $$R_3COX \quad (III)$$

in which
$R_3$ has the meaning given for formula I and
X is, for example, OH, Cl or Br,
to give compounds of the formula $$R_1-CONH-(CH_2)_m-NH-CH_2CH_2-N-(CH_2)_n-NHCO-R_2 \quad (IV)$$
$$\underset{R_3}{\overset{CO}{|}}$$

in which $R_1$, $R_2$, $R_3$, m and n have the meanings given for formula I,
and the imidazoline ring is then closed using acids HA, in which A has the meaning given for formula I.

The new compounds are used as softeners for knitted textiles, woven textiles or non-woven textiles of natural and synthetic fibres, and for paper and leather. They are preferably employed in the form of readily water-soluble flakes, and in aqueous, organic or aqueous/organic, in particular concentrated organic, solution, and the solution can contain further emulsifiers, water repellants and/or optical brighteners. Furthermore, the use of the new compounds as constituents in pulverulent or liquid detergents, which contain an optical brightener if appropriate, is noteworthy.

By the chain lengths of the radicals $R_1$, $R_2$ and $R_3$ in formula I, many properties of the softeners can be influenced in the desired direction, such as ready solubility, substantial hydrophilic character of the finished goods, improved application from short liquor, improved exhaustion behaviour from long liquor, very soft handle of the finished goods, very low sensitivity to hardness, low sensitivity to pH, high brittleness for flaking the product, and ready solubility of the flaked product.

A further advantage of the softeners according to the invention is the small effect on the degree of whiteness of brightened goods or goods which have been rebrightened and resoftened in the washing process. Solutions which contain optical brighteners can therefore readily be prepared using these softeners, without the degree of whiteness being substantially effected in the treatment of the textiles.

EXAMPLE 1

540 g of stearic acid (2 mols of an industrial tallow fatty acid mixture, acid number=207) and 146 g of triethylenetetramine (1 mol) are heated to about 175° C. under a nitrogen atmosphere. 36 g of water split off, and are distilled off in the absence of a vacuum. IR analysis indicates the formation of the 1,ω-acyl derivative, without showing an imidazoline band at 6.4μ. 120 g of acetic acid are allowed to run into the mixture, and more water is distilled off at 175°–185° C. After about 2 hours, the distillate is tested for acetic acid. The amount determined is reintroduced into the reaction mixture, and the reaction is carried through to the end. The end product which readily solidifies can be processed on a cooling roll to give flakes. These dissolve readily in cold water to give a 1:10 dilute solution when cold water is poured over the flakes, and the mixture is allowed to stand for several hours and is then stirred for a short time until homogeneous.

It is not possible to obtain evidence for the ring closure from the IR spectrum, since the characteristic band is overlapped by the acid amide bands. In contrast, the appearance of a new maximum or of a very pronounced shoulder at 230–232 nm in the UV spectrum is certain eveidence of the 1,2,3-substituted imidazoline ring.

EXAMPLE 2

10 g of the product from Example 1 are sprinkled in 90 g of water of 17° German hardness and at 18°–20° C. After a stirring time of 15 minutes, the flakes in the vessel are thoroughly distributed and wetted. The stirring unit is switched off. After a swelling and dissolving process of 8 hours, the stirring unit is switched on for 10 minutes, and the emulsion is homogenised.

The resulting emulsion shows no precepitations and/or undissolved constituents, and can be employed as a softening agent for textiles.

EXAMPLE 3

200 g of knitted cotton goods are dyed with reactive dyestuffs in a laboratory jet-dyeing apparatus, according to known processes, are then soaped, and are rinsed several times with hot and cold water, and left in the last rinsing liquor. 4 g of the 10% strength emulsion according to Example 2 are then poured into 100 c cm of water at 35° C. and are distributed by stirring gently.

The 4 g of emulsion correspond to 2% of softening agent, relative to the weight of the goods.

This solution is poured into the mixture vessel and is rinsed into the jet-dyeing apparatus. During a treatment time of 20 minutes at 35° C., only minimum amounts of foam are formed, which do not adversely affect the passage of the goods. Precipitations, for example breaking of the emulsion, as a result of the high shearing force effect of the pump are not observed. After the end of the treatment time, the liquor is discharged, and the goods are removed and are dewatered to 25% residual moisture in a domestic centrifuge. The textile is dried in a drying cabinet at 120° C. with air circulated by ventilators.

After conditioning for 24 hours at 65% residual moisture, the material sample is evaluated.

(A) Handle: pleasant soft voluminous handle.

(B) Hydrophiic character: 0.5 ccm of distilled water are introduced dropwise onto the fabric by means of a pipette, and the penetration time is determined: conventional cationic softening agent based on distearyldimethylammonium chloride: penetration time 60-180 seconds; product according to the invention: penetration time 25-35 seconds.

EXAMPLE 4

Cotton terry fabric is treated, in a winch vat, with a commercially available anionic whitener based on stilbenedisulphonic acid. Thereafter, the fabric is rinsed for a short time, and 1.5% of the weight of the goods of the 10% strength emulsion according to Example 2, which is poured into 100 ccm of water at 35° C. and is distributed by gentle stirring, is added to the rinsing bath. After the end of the treatment, the fabric is centrifuged, dried at 120° C., and conditioned.

In contrast to the treatment with a commercially available softening agent based on distearyldimethylammonium chloride (change of shade to yellow), a substantially smaller effect on the degree of whiteness occurs in the treatment, described above, with the softener according to the invention (see also Table 1).

EXAMPLE 5

In a yarn-dyeing apparatus, high-bulk polyacrylonitrile yarn is dyed and rinsed. 3% (relative to the weight of the yarn) of the preparation obtained according to Example 2 is diluted with water and added to the rinsing bath. After 20 minutes at a treatment temperature of 35° C., the yarn is centrifuged, and is dried at 120° C. After the conditioning for 24 hours at 65% residual moisture, the surface resistivity ($R_{OT}$) was measured according to DIN (German Industrial Standard) 53,345, sheet 1: $2.5 \times 10^8$ Ohm. Sufficient antielectrostatic character for further processing (for example weaving and knitting) as well as for comfort during wear is thus provided.

EXAMPLE 6

As shown in Table 1 below, the degree of brightening is substantially reduced when a wash which has been washed and brightened using a commercially available pulverulent detergent is after-treated with a commercially abailable softening agent based on distearyldimethylammonium chloride. Even the addition of a commercially available softener based on stibenedisulphonic acid does not eliminate this effect completely. When the wash is after-treated with the softener according to the invention and obtained according to Example 1, the brightening effect is scarcely adversely affected; when a commercially available brightener is added, even a further increase in the brightening effect occurs.

TABLE 1

| | Degree of whiteness (W 6') on bleached cotton fabric (W 6' = 41) | | | | |
|---|---|---|---|---|---|
| Wash cycles | Washed with 5 g/l of A | After-treated with 2 g/l of B | After-treated with 2 g/l of B + 0.5% of C | After-treated with 2 g/l of D | After-treated with 2 g of D + 0.5% of C |
| 1 × | 133 | 93 | 96 | 123 | 43 |
| 2 × | 167 | 129 | 148 | 165 | 75 |

A = commercially available pulverulent detergent containing optical brighteners (Omo (®(R))
B = commercially available softening agent based on distearyldimethylammonium chloride
C = anionic whitener based on stilbenedisulphonic acid
D = softening agent according to the invention, according to Example 1

EXAMPLE 7

When the softener according to the invention, from Example 1, is added to a liquid detergent, a further increase in the degree of whiteness is observed, in contrast to a commercially available softener (see Table 2).

TABLE 2

| | Degree of whiteness (WG 6') on bleached cotton fabric (WG 6' = 41) | | |
|---|---|---|---|
| Wash cycles | Washed with E | Washed with E containing 7.5% of B | Washed with E containing 7.5% of D |
| 1 × | 149 | 144 | 149 |
| 3 × | 167 | 164 | 173 |

E = liquid detergent containing 25% of a non-ionic surfactant, 4% of triethanolamine, 11% of ethanol, 15% of an anionic surfactant and 0.5% of a whitener based on stilbenedisulphonic acid
B = commercially available detergent based on distearyldimethylammonium chloride
D = softening agent according to the invention, according to Example 1

EXAMPLE 8

621 g of stearic acid (2.3 mols of an industrial tallow fatty acid mixture, acid number = 207) and 146 g of triethylenetetramine (1 mol) were reacted according to the conditions of Example 1. 102 g (= 1.7 mols) of acetic acid were employed. The cyclisation is carried out under the conditions of Example 1. In this product, $R_3$ is divided into 0.7 mol of $CH_3$ and 0.3 mol of $C_{17}H_{35}$ groups. 24 g of phosphorous acid are dissolved in the product before it has cooled, and flakes are then produced on a cooling roll. A brittle, pale and readily soluble softener is obtained (6.4μ (IR)).

After a polyamide monofilament has been finished, a static friction of 0.07 is measured, while distearyldimethylammonium chloride gives a value of 0.14 under the same conditions (filament-filament friction).

What is claimed is:

1. An imidazoline derivative of the formula $$R_1-CONH-(CH_2)_{\overline{m}}-N\overset{\oplus}{\underset{R_3}{\diagdown\diagup}}N-(CH_2)_{\overline{n}}-NHCO-R_2 \quad A^{\ominus}$$

in which
$R_1$, $R_2$ and $R_3$ each independently is $C_1-C_{19}$-alkyl or $C_{2-19}$-alkenyl,
m and n each independently is 2 or 3, and $A^{\ominus}$ is an anion.

2. A compound according to claim 1, in which $A^{\ominus}$ is an anion selected from the group consisting of formate, acetate, phosphate, phosphite, phosphonate, sulphonate, toluenesulphonate and benzoate.

* * * * *